United States Patent [19]

Kummer et al.

[11] Patent Number: 4,950,797

[45] Date of Patent: Aug. 21, 1990

[54] PREPARATION OF CARBONYL COMPOUNDS BY ISOMERIZATION OF ALLYL ALCOHOLS

[75] Inventors: Rudolf Kummer, Frankenthal; Werner Bertleff, Viernheim; Michael Roeper, Wachenheim, all of Fed. Rep. of Germany

[73] Assignee: BASF Aktiengesellschaft, Ludwigshafen, Fed. Rep. of Germany

[21] Appl. No.: 201,064

[22] Filed: Jun. 1, 1988

[30] Foreign Application Priority Data

Jun. 5, 1987 [DE] Fed. Rep. of Germany ....... 3718897

[51] Int. Cl.$^5$ ............................................. C07C 45/00
[52] U.S. Cl. ..................... 568/450; 568/341; 568/375; 568/384; 568/420; 568/443; 568/448; 568/496; 568/414; 568/376; 560/126; 560/174
[58] Field of Search ................ 560/174, 126; 568/414, 568/376, 384, 375, 341, 443, 450, 420, 448, 496

[56] References Cited

U.S. PATENT DOCUMENTS 4,117,016  9/1978  Hughes .............................. 568/384

OTHER PUBLICATIONS

Derwent Abstracts: JP 5377/66 (Toyo Rayon), 25.3.66, Production of Carbonyl Compounds.
J. Organometallic Chemistry, 86, C17 (1975).
J. Falbe, New Syntheses with Carbon Monoxide, Springer, Berlin (1980), pp. 107–108.
Bull. Soc. Chim. France, No. 1, 668 (1950).
J. Am. Chem. Soc., 74, 5324 (1952).
S. G. Davies, Organo-Transition-Metal Chemistry, Applications to Organic Synthesis, Pergamon, Oxford (1982), pp. 282–284.

*Primary Examiner*—Paul J. Killos
*Attorney, Agent, or Firm*—John H. Shurtleff

[57] ABSTRACT

A process for the preparation of carbonyl compounds by catalyzed isomerization of allyl alcohols in a tertiary phosphine or phosphite ester in the presence of a rhodium compound at a temperature of from 80° C. to 180° C., a carrier gas being passed through the reaction mixture and the carbonyl compound being separated from the emergent gas mixture by cooling.

10 Claims, No Drawings

PREPARATION OF CARBONYL COMPOUNDS BY ISOMERIZATION OF ALLYL ALCOHOLS

The present invention relates to a novel process for the preparation of carbonyl compounds by catalyzed isomerization of allyl alcohols.

4-Hydroxybutyraldehyde can be prepared by acid-catalyzed hydration of 2,3-dihydrofuran as given in *Bull. Soc. Chim. France*, No. 1, 668 (1950) or by ozonolysis of 4-penten-1-ol as given in *J. Am. Chem. Soc.*, 74, 5324 (1952), for example, but these are methods that are not suitable for preparing the compound on the industrial scale.

Aldehydes have been obtained by catalyzed isomerization of allyl alcohols before. For instance, it is known from S. G. Davies, Organo-transition-metal Chemistry, Applications to Organic Synthesis, Pergamon, Oxford (1982), pp. 282-4 that allyl alcohol and methylallyl alcohol rearrange to propionaldehyde and isobutyraldehyde respectively in the presence of metal complexes. However, these processes yield mixtures from which the aldehyde can be isolated only by elaborate methods.

Rhodium catalysts have also been used already for the isomerization of allyl alcohols to aldehydes. According to *J. Organomet. Chem.*, 86, C17 (1975) methylallyl alcohol rearranges to isobutyraldehyde in the presence of the complex $[RhH(CO)\{(C_6H_5)_3P\}_3]$. The reaction is highly dependent on the nature of the solvent; in the expensive solvent trifluoroethanol rearrangement is complete in 3 hours at a temperature of 70° C. No information is given about isolation of the aldehyde or whether the catalyst can be employed a second time. This process too has found no industrial applications.

Isomerization of allyl alcohols to aldehydes has been observed as an unwanted side reaction accompanying hydroformylation of allyl alcohols—cf. J. Falbe, *New Syntheses with Carbon Monoxide*, Springer, Berlin (1980), pp. 107-8. It occurs particularly when cobalt catalysts are used, so that, for instance, propionaldehyde is formed as well as 4-hydroxybutyraldehyde and 3-hydroxy-2-methylpropionaldehyde when allyl alcohol is hydroformylated. Attempts to isolate pure 4-hydroxybutyraldehyde from the mixtures result in large reductions in yield because this compound tends to undergo condensation. If however, catalyst systems consisting of rhodium compounds and phosphines are used the double-bond isomerization that is an undesirable accompaniment to hydroformylation is repressed; cf. *Chem.-Ztg.*, 101, 343-50 (1977).

We have found that carbonyl compounds can be prepared particularly well by catalytic isomerization of allyl alcohols in the presence of a rhodium compound at a temperature of from 80° C. to 180° C. if the reaction is carried out in a liquid reaction mixture consisting essentially of a molten tertiary phosphine or phosphite ester, a carrier gas is passed through the mixture, and the vapor of the carbonyl compound entrained in the gas stream is condensed.

The novel process permits almost quantitative conversion of allyl alcohols, selective formation of aldehydes, and particularly simple isolation of the products. This advantageous result is unexpected, since it is known that the introduction of phosphines suppresses rearrangement of allyl alcohols when they are hydroformylated in the presence of rhodium complexes.

By means of the novel process carbonyl compounds of the general formula I can be prepared from allyl alcohols of the general formula II,

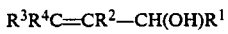

where $R^1$ and $R^4$ are either separately hydrogen or methyl or together a saturated or olefinic hydrocarbon chain of from 3 to 6 carbon atoms, $R^2$ is hydrogen, methyl, or alkoxycarbonyl, and $R^3$ is hydrogen, methyl, or hydroxymethyl.

Allyl alcohols of the general formula II include allyl alcohol, methylallyl alcohol, 2-cyclohexen-1-ol, 2,7-octadien-1-ol, 3,7-dimethyl-2,6-octadien-1-ol (geraniol, nerol), 3-methyl-2-buten-1-ol, 2-butene-1,4-diol, 2-methyl-2-butene-1,4-diol, and methyl 3-hydroxy-2-methylenebutyrate. The novel process is particularly suitable for the preparation of 4-hydroxybutyraldehyde from 2-butene-1,4-diol.

Suitable rhodium compounds include: hydridocarbonyltris(triphenylphosphine)rhodium, $[RhH(CO)\{(C_6H_5)_3P\}_3]$; acetylacetonatodicarbonylrhodium, $[Rh(acac)(CO)_2]$; rhodium acetate; rhodium nitrate; chlorocarbonylbis(triphenylphosphine)rhodium, $[RhCl(CO)\{(C_6H_5)_3P\}_3]$; chlorotris(triphenylphosphine), $[RhCl\{(C_6H_5)_3P\}_3]$; rhodium chloride. All other rhodium compounds that dissolve in the reaction mixture and can form rhodium hydride complexes under the conditions of the reaction are also suitable.

The preferred tertiary phosphine is triphenylphosphine, but suitable phosphines include all those of the general formula $PAr_{3-n}R_n$, where Ar is an aryl radical, such as phenyl, R is an alkyl or cycloalkyl radical, and n is an integer of from 1 to 3 or zero. Suitable phosphites include those esters of the general formula $P(OAr)_{3-n}(OR)_n$, where Ar is an aryl radical, such as phenyl, R is an alkyl radical, and n is an integer of from 1 to 3 or zero.

The molar ratio of the amount of phosphine or phosphite ester to the amount of rhodium compound is arranged to be between, for example, 3:1 and 5000:1, but the preferred range is from 50:1 to 500:1.

In the novel process the allyl alcohol is made to rearrange in a mixture of the phosphine or phosphite and the rhodium compound at temperatures of from 80° C. to 180° C., preferably from 100° C. to 150° C. It is expedient to mix the phosphorus and rhodium compounds, heat the mixture to the required reaction temperature, forming a melt in which the rhodium compound is dissolved, and then add the allyl alcohol while passing a carrier gas through the mixture. The carbonyl compound formed bt rearrangement is entrained in the gas stream as vapor and is subsequently isolated by cooling. Preferably the allyl alcohol is added to the melt at a rate such that conversion is as complete as possible and the carbonyl compound is removed at the same rate as it is formed. The carrier gas can be recirculated through the melt once the carbonyl compound has been removed by condensation.

The gases that can be used as carrier gases include nitrogen, carbon monoxide, methane, hydrogen, and mixtures of any of these. Particularly good results are obtained with hydrogen or a mixture containing hydrogen; for instance, the volume fraction of hydrogen in the carrier gas can be from about 0.1% to 100%, the remainder being carbon monoxide, nitrogen, argon, or methane.

The carbonyl compound separated from the gas stream by condensation can if necessary be obtained in high purity by simple distillation.

EXAMPLE 1

A mixture of 5.0 g of rhodium acetate (19.3 mmol) and 80 g of triphenyl phosphine (310 mmol) was heated to a temperature of 130° C. in a thermostatted glass vessel and a 1:1-mixture by volume of carbon monoxide and hydrogen was passed through the melt via a sintered-glass distributor at the rate of 100 l/h. After 2 h the gas flow was increased to 120 l/h and 356 ml (380 g) of 2-butene-1,4-diol was added over a period of 7 h (50.9 ml/h). The stream of gas and vapor was passed through a water-cooled condenser and a trap cooled by acetone and solid carbon dioxide.

The condensate weighed 370 g, and gas chromatography showed that it contained 90.5% of 4-hydroxybutyraldehyde, 2.1% of 1,4-butanediol, and less than 0.1% of 2-butene-1,4-diol. The conversion was 99.9%, the selectivity 90.5%.

EXAMPLE 2

In the apparatus described in Example 1 a 1:1-mixture by volume of carbon monoxide and hydrogen was passed at the rate of 164 l/h through a molten mixture of 1.0 g of hydridocarbonyltris(triphenylphosphine)rhodium (1.1 mmol) and 80 g of triphenylphosphine (310 mmol) heated to a temperature of 130° C. Over a period of 58 h 1120 ml (1195 g) of 2-butene-1,4-diol was added (19.3 ml/h).

The condensate weighed 1076 g, and gas chromatography showed that it contained 77.2% of 4-hydroxybutyraldehyde, 1.3% of 1,4-butanediol, and 14.2% of 2-butene-1,4-diol. The conversion was 85.8%, the selectivity 90.0%.

The experiment was continued with a higher gas flow, 213 l/h, and over a period of another 60 h a further 998 ml (1065 g) of 2-butene-1,4-diol was added (16.7 ml/h).

This time the condensate weighed 1025 g, and gas chromatography showed that it contained 59.2% of 4-hydroxybutyraldehyde, 0.7% of 1,4-butanediol, and 26.1% of 2-butene-1,4-diol. The conversion was 73.9%, the selectivity 80.1%.

The catalyst thus continued to display high activity over a period of 118 h.

EXAMPLE 3

A melt was prepared as described in Example 2 and through it was passed hydrogen at the rate of 193 l/h. Over a period of 20.5 h 399 ml (426 g) of 2-butene-1,4-diol was added (19.5 ml/h).

The condensate weighed 370 g, and gas chromatography showed that it contained 72.6% of 4-hydroxybutyraldehyde, 1.9% of 1,4-butanediol, and 9.2% of 2-butene-1,4-diol. The conversion was 90.8%, the selectivity 80.0%.

EXAMPLE 4

The experiment described in Example 3 was continued with a 1:1-mixture by volume of hydrogen and nitrogen flowing at the rate of 108 l/h as carrier gas. Over a period of 7.5 h 145 ml (157 g) of 2-butene-1,4-diol was added (19.3 ml/h).

The condensate weighed 160 g, and gas chromatography showed that it contained 76.5% of 4-hydroxybutyraldehyde, 1.5% of 1,4-butanediol, 8.3% of 2-butene-1,4-diol. The conversion was 91.7%, the selectivity 83.4%.

EXAMPLE 5 (COMPARISON)

A 250-ml distillation flask was fitted with a 1-m Vigreux column and supplied with a capillary boiling aid. A mixture of 3.0 g of hydridocarbonyltris(triphenylphosphine)rhodium (3.3 mmol), 50 g of triphenylphosphine (190 mmol), and 150 g of 2-butene-1,4-diol was heated in the flask to a temperature of from 120° C. to 125° C. under a pressure of 1 mm Hg. Within a short time 50.0 g of distillate passed over, the temperature at the head of the column rising from 40° C. to 50° C. After that no more distillate was seen to form, although only about a third of the 2-butene-1,4-diol had been converted.

Gas chromatography showed that the distillate contained 91.4% of 4-hydroxybutyraldehyde, 0.4% of 1,4-butanediol, and 0.5% of 2-butene-1,4-diol.

The experiment showed that in the absence of a carrier gas containing hydrogen the required isomerization does take place with high selectivity, but the catalyst soon loses its activity.

EXAMPLE 6

In the apparatus described in Example 1 a mixture of 3.0 g of hydridocarbonyltris(triphenylphosphine)rhodium (3.3 mmol) and 60 g of triphenylphosphine (230 mol) was heated under nitrogen to a temperature of 135° C. A 1:1-mixture by volume of carbon monoxide and hydrogen was passed through the melt at a rate of 100 l/h and allyl alcohol was added at the rate of 80 g/h.

After 30 min 38 g of condensate had collected, and gas chromatography showed that it contained 23% of propionaldehyde and 75% of allyl alcohol. The conversion was 25%, the selectivity 92%.

EXAMPLE 7

After the end of the experiment described in Example 1 a 1:1-mixture by volume of carbon monoxide and hydrogen was passed through the melt at the rate of 150 l/h for 2 h, the temperature being kept at 130° C., removing the last traces of 2-butene-1,4-diol and 4-hydroxybutyraldehyde. With the same temperature and gas flow 2-cyclohexen-1-ol was added at the rate of 20 g/h.

After 1 h 19 g of condensate had collected; it contained 2.5% of cyclohexanone and 82% of 2-cyclohexen-1-ol. The conversion was 18%, the selectivity 14%. There was approximately a 10% yield of 3-cyclohexen-1-ol.

EXAMPLE 8

In the apparatus described in Example 1 a mixture of 2.0 g of hydridocarbonyltris(triphenylphosphine)rhodium (2.2 mmol) and 80 g of triphenylphosphine was heated to a temperature of 130° C. and a 1:4-mixture by volume of hydrogen and nitrogen was passed through the melt at the rate of 160 l/h. 2-Methyl-2-butene-1,4-diol was added at the rate of from 20 ml/h to 25 ml/h.

After 6 h 100 g of condensate had collected, and gas chromatography showed that it contained 65.9% of 4-hydroxy-3-methylbutyraldehyde and 4.1% of 4-hydroxy-2-methylbutyraldehyde as the cyclic semiacetals and 30% of 2-methyl-2-butene-1,4-diol. The conversion was 70%, the selectivities 94.1% and 5.9%.

EXAMPLE 9

In the apparatus described in Example 1 a mixture of 5.0 g of hydridocarbonyltris(triphenylphosphine)rhodium (5.4 mmol) and 80 g of triphenylphosphine was heated to a temperature of 130° C. and a 1:1-mixture by volume of carbon monoxide and hydrogen was passed through the melt at the rate of 195 l/h. Methyl 3-hydroxy-2-methylenebutyrate was pumped in at the rate of 21 ml/h.

Condensate collected at the rate of 19.5 ml/h, and gas chromatography showed that it contained 35.8% of methyl 2-methyl-3-oxobutyrate, 41.3% of methyl 2-methyl-2-butenoate, and 19.5% of methyl 3-hydroxy-2-methylenebutyrate. The conversion was 80.5%, the selectivity 44.5%.

EXAMPLE 10

The experiment described in Example 9 was repeated with a 6:94-mixture by volume of hydrogen and nitrogen flowing at the rate of 196 l/h as carrier gas.

The condensate contained 72.7% of methyl 2-methyl-3-oxobutyrate, 4.8% of methyl 2-methyl-2-butenoate, and 21.7% of methyl 3-hydroxy-2-methylenebutyrate. The conversion was 78.3%, the selectivity 92.8%.

EXAMPLE 11

In the apparatus described in Example 1 a mixture of 2.3 g of hydridocarbonyltris(triphenylphosphine)rhodium (2.5 mmol) and 65 g of triphenylphosphine (250 mmol) was heated to a temperature of 130° C. and a 1:9-mixture by volume of hydrogen and nitrogen was passed through the melt at the rate of 90 l/h. 2,7-Octadien-1-ol was pumped in at the rate of 17 ml/min.

After 1 h the condensate weighed 12.6 g, and gas chromatography showed that it contained 49.6% of mixed octenals, 20.2% of 2,7-octadien-1-ol, and 30.2% of mixed octadien-1-ols. The conversion was 79.8%, the selectivity 62.2%.

EXAMPLE 12

The experiment described in Example 2 was repeated with argon flowing at 155 l/h as carrier gas. 2-Butene-1,4-diol was added at the rate of 30 ml/h.

After 8.5 h the inflow of 2-butene-1,4-diol was interrupted for 3.5 h, because the level of liquid in the vessel had risen. When the original level was regained, 2-butene-1,4-diol was again added at the rate of 30 ml/h, but the level again rose and inflow was interrupted after 1 h for a further 2.5 h. Inflow was resumed at the same rate for another 1 h, but since no more condensate collected the experiment was broken off after a total of 19.5 h. The total quantity of 2-butene-1,4-diol added was 340 ml (363 g).

The condensate contained 180 g of 4-hydroxybutyraldehyde and 148 g of 2-butene-1,4-diol. The conversion was 59.2%, the selectivity 83.7%.

The experiment showed that the required isomerization took place when carrier gas free from hydrogen was used, and that selectivity was high, but the activity of the catalyst dropped off after about 20 h.

We claim:

1. In a process for the preparation of a carbonyl compound of the formula $$R^3R^4HC-CHR^2-C(=O)R^1 \qquad I$$

where $R^1$ and $R^4$ are either separately hydrogen or methyl or together a saturated or olefinic hydrocarbon chain of from 3 to 6 carbon atoms, $R^2$ is hydrogen, methyl, or alkoxycarbonyl, and $R^3$ is hydrogen, methyl or hydroxymethyl, by catalyzed isomerization of an allyl alcohol of the formula $$R^3R^4C=CR^2-CH(OH)R^1 \qquad II$$

in the presence of a rhodium compound at elevated temperatures, the improvement which comprises:
heating the allyl alcohol in a liquid reaction mixture consisting essentially of a molten tertiary phosphine or phosphite ester containing the rhodium compound dissolved therein in a molar ratio of the tertiary phosphine or phosphite ester to the rhodium compound of between 3:1 and 5000:1, at a temperature of from 80° C. to 180° C.;
passing a carrier gas through the reaction mixture; and
condensing the vapor of the carbonyl compound entrained in the gas stream by cooling.

2. A process as claimed in claim 1 wherein the carrier gas is hydrogen or a gas containing hydrogen.

3. A process as claimed in claim 1 wherein the allyl alcohol is added to the heated melt of tertiary phosphine or phosphite ester containing said rhodium compound at the same rate as the carbonyl compound formed is removed from the reaction mixture in the stream of carrier gas.

4. A process as claimed in claim 1 wherein 4-hydroxybutyraldehyde is prepared from 2-butene-1,4-diol.

5. A process as claimed in claim 1 wherein the tertiary phosphine is a compound of the formula $PAr_{3-n}R_n$ and the phosphite ester is a compound of the formula $P(OAr)_{3-n}(OR)_n$, Ar being an aryl radical, R an alkyl radical, and n an integer of from 1 to 3 or zero.

6. A process as claimed in claim 1 wherein the rhodium compound is selected from the group consisting of: hydridocarbonyltris(triphenylphosphine)rhodium, [RhH(CO){(C$_6$H$_5$)$_3$P}$_3$]; acetylacetonatodicarbonylrhodium, [Rh(acac)(CO)$_2$]; rhodium acetate; rhodium nitrate; chlorocarbonylbis(triphenylphosphine)rhodium, [RhCl(CO){(C$_6$H$_5$)$_3$P}$_3$]; chlorotris(triphenylphosphine), [RhCl{(C$_6$H$_5$)$_3$P}$_3$]; rhodium chloride.

7. A process as claimed in claim 1 wherein the ratio of the amount of tertiary phosphine or phosphite ester to the amount of rhodium compound is between 50:1 and 500:1.

8. A process as claimed in claim 7 using a tertiary phosphine of the formula $PAr_{3-n}R_n$ wherein Ar is aryl, R is alkyl and n is an integer of from 1 to 3 or zero.

9. A process as claimed in claim 7 using a phosphite ester of the formula $P(OAr)_{3-n}(OR)_n$ wherein Ar is aryl, R is alkyl and n is an integer of from 1 to 3 or zero.

10. A process as claimed in claim 2 wherein the volume fraction of hydrogen in the carrier gas is from about 0.1% to 100%.

* * * * *